United States Patent [19]

Moore

[11] Plant 4,479

[45] Nov. 6, 1979

[54] MINIATURE ROSE PLANT

[76] Inventor: Ralph S. Moore, 2519 E. Noble Ave., Visalia, Calif. 93277

[21] Appl. No.: 965,522

[22] Filed: Dec. 1, 1978

[51] Int. Cl.[2] ..... A01H 5/00

[52] U.S. Cl. ..... Plt./9

[58] Field of Search ..... Plt./7, 9

*Primary Examiner*—Robert E. Bagwill

[57] ABSTRACT

The subject of the present disclosure is a new and distinct variety of miniature rose plant characterized by the abundance of small double pink flowers and by the bushy spreading growth habit.

1 Drawing Figure

The present invention relates to a new and distinct variety of hardy, dwarf, bush type rose plant of the miniature class; the variety being primarily characterized—as to novelty—by soft pink to rose pink buds and flowers which in general color effect are similar to Eleanor, miniature (U.S. Plant Pat. No. 2,175).

The variety is further characterized by:

An abundance of bloom, with flowers usually borne several to the stem in loose clusters.

Little or no fragrance.

A plant which is vigorous, of rounded somewhat spreading shape with semi-glossy small foliage with pointed leaflets; the buds and flowers being similar in form and size to June Time (miniature—U.S. Plant Pat. No. 2,563).

The plant, which has a normal height of 10–12 inches and a mature spread of 24–30 inches, can easily be maintained at lesser size by occasional trimming.

A plant which grows and blooms satisfactorily both in greenhouse and outdoors; is good for growing in pots or hanging baskets; and provides excellent garden decoration as well as cut flowers.

The present variety of miniature rose was originated by me at Sequoia Nursery located at Visalia, Calif., under conditions of careful control and observation, as a cross between an un-named seedling (Rosa Wichuriana × Floradora) not patented as the seed parent and Sheri Anne (miniature—U.S. Plant Pat. No. 3,826), as the pollen parent.

Subsequent to origination of the variety I successfully reproduced it, at Sequoia Nursery, located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; spreading; seedling; greenhouse; outdoors; cut flowers; garden decoration; potted plant.

Class: Miniature. Variety name: Happy Thought.

Flowers borne: Usually several together in clusters of 3–5 or more on slender wirey stems.

Quantity of bloom: Abundant both outside and in greenhouse.

Bud:

*Peduncle.*—Medium length; slender but sturdy; erect; medium green, often tinted bronze (outdoors); Hairs — fairly numerous (similar to peach fuzz).

*Before calyx breaks.*—Size — small. Form short; pointed with several small foliaceous apendages and numerous tiny hairs (like fuzz) on surface of bud; with foliaceous parts extending beyond the tip of the bud equal to one-half or less of its length. Color — medium green, often tinted with bronze (outdoors).

*As calyx breaks.*—(A) Color — in greenhouse, medium pink — near Carmine Rose 621 and (B) Outdoors (November 1978) — shades of red — near Blood Red 820/2 sometimes overlaid with areas of darker red, with pale greenish or white area at base.

*Opening.*—Opens well in all weather.

Bloom:

*Size when fully open.*—Small, averaging about 30–35 mm (1¼").

*Petalage.*—Double — averaging about 45–55 petals, arranged regularly plus sometimes several small petaloids.

*Form.*—Cupped at first, becoming more rounded in the center, with petals reflexing loosely outward and later at maturity, rolled loosely outward and downward. Less double flowers may show stamens and pistils.

Petals: Fairly thin; satiny on inside and on outside surface.

*Shape.*—Outside petals — broad lanceolate with rounded tip plus very small (short) acute tip; Intermediate — broad lanceolate with rounded tip plus very small (short) acute tip; Inside — lanceolate with acute tip.

Color: Newly opened flower from a plant grown indoors (plastic house), November 1978, Visalia, Calif.:

*Outside petals.*—Outside surface — near Carmine Rose 621 and 621/1 with small white area at base. Inside surface — near Carmine Rose 621 and 621/1 with small near white area at base.

*Intermediate petal.*—Outside surface — similar to outside petal but with near white to yellow at base. Inside surface — similar to outside petal, but with near white to yellow at base.

*Inner petal.*—Outside surface — similar to intermediate petal; Inside surface — similar to intermediate petal.

*General color effect.*—Newly opened flowers — soft pink to rose pink. Three days open — color (in greenhouse) similar to newly opened flowers but less brilliant (see behavior).

*Behavior.*—Open well in all weather. Color lasts well and (outdoors) may become darker with age (near Neyron Rose 623/1 shading or blending into darker rose near petal tips). Spent petals drop off. Flower longevity (May 1978) — plant in pot 6–8 days or longer. Cut flowers at living room temperature 3 to 5 days or longer.

Reproductive organs:

*Stamens.*—May or may not be present, arranged regularly about pistils.

*Filaments.*—Varying length; fairly long, yellow.

*Anthers.*—(When present) well formed; yellow.

*Pollen.*—Little or none.

*Pistils.*—Average number.

*Styles.*—Fairly even; medium to long; bunched; color — near white.

*Stigmas.*—Near white .

*Ovaries.*—All enclosed in calyx.

*Hips.*—None.

*Sepals.*—Permanent; spear shaped; recurved against peduncle.

*Seed.*—None.

Foliage:

*Leaves.*—Compound of five (sometimes three or seven); leaflets; fairly small; leathery; semi-glossy.

*Leaflets.*—Shape: nearly oval; apex acute; base rounded or rounded acute. Margin serrate. Color: medium green; new growth — normal (medium) green (outdoors — foliage darker green; new growth bronzy). Rachis: medium strength; upper side may have a few tiny short prickles or hairs, grooved; underside sparsely thorny with few or no tiny prickles or hairs.

Stipules: medium long; narrow to medium width; medium length; narrow points which turn out usually at about 45 degrees.

Growth:

*Habit.*—Dwarf; bushy; rounded; spreading; much branched.

*Growth.*—Free vigorous; internodes short.

*Canes.*—Medium; slender; willowy.

*Main stems.*—Color: medium green.

*Thorns.*—Average; slender; nearly straight; may be slightly hooked or inclined slightly downward; color: brown. Prickles — none. Hairs — none.

*Branches.*—Color: medium green. Thorns: moderate number; medium length; slender; nearly straight, inclined downward. Medium oval base. Prickles: none.

*Hairs.*—None.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, spreading, much branched habit, substantially as illustrated and described, characterized by buds and flowers of a soft pink to rose pink color, being of a shade generally near Carmine Rose 621/1, the bud and flower resembling the variety June Time (U.S. Plant Pat. No. 2,563) in form and size; and further characterized by a plant of vigorous and compact growth habit, easy to propagate from cuttings or by budding, with an abundance of small to medium size semi-glossy foliage and an abundance of flowers borne usually in loose clusters of 3 to 5 or more.

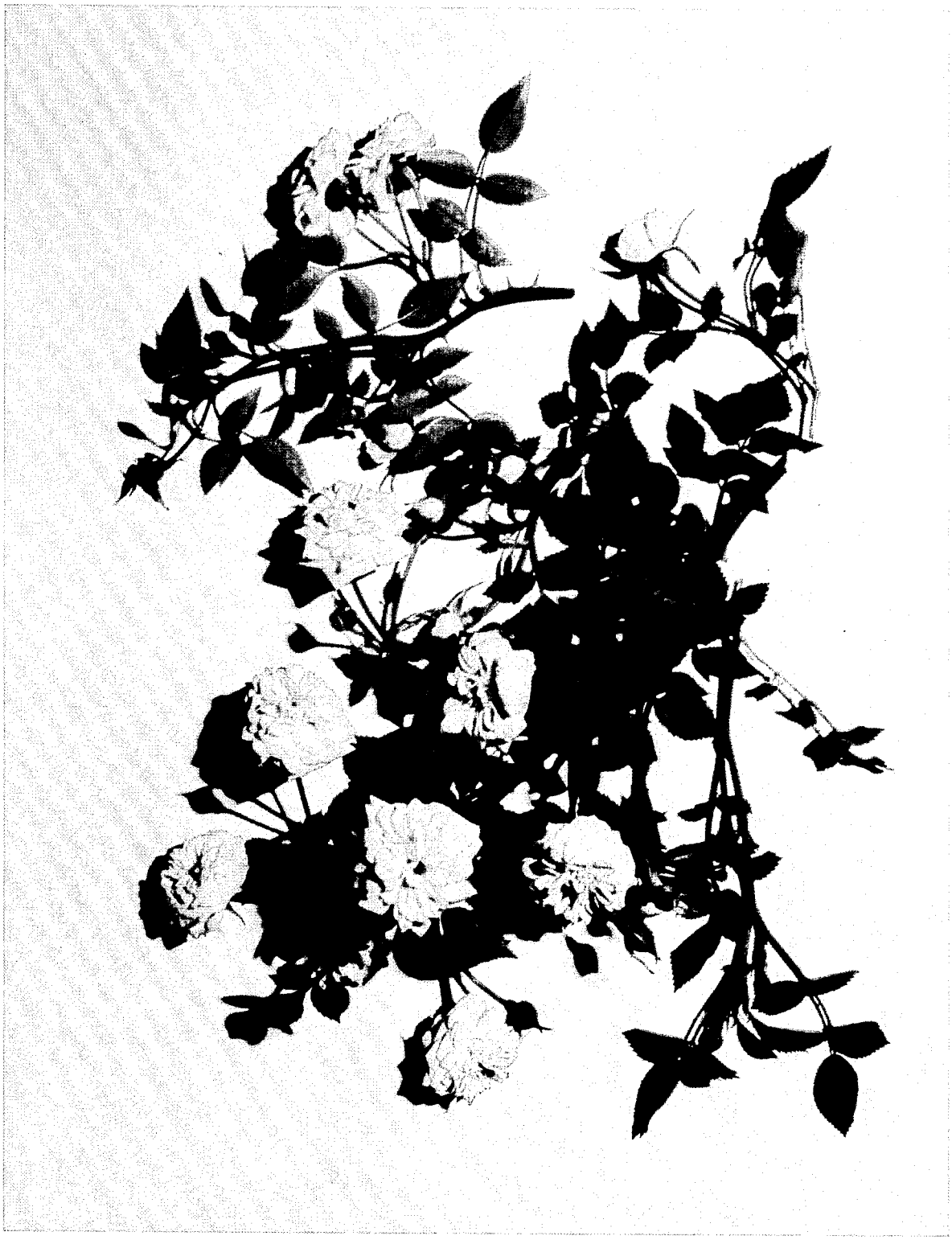

* * * * *